US005616457A

United States Patent [19]

García-Rubio

[11] Patent Number: 5,616,457

[45] Date of Patent: Apr. 1, 1997

[54] METHOD AND APPARATUS FOR THE DETECTION AND CLASSIFICATION OF MICROORGANISMS IN WATER

[75] Inventor: Luis H. García-Rubio, Temple Terrace, Fla.

[73] Assignee: University of South Florida, Tampa, Fla.

[21] Appl. No.: 385,539

[22] Filed: Feb. 8, 1995

[51] Int. Cl.$^6$ .............................. C12Q 1/00; C12Q 1/04; C12Q 1/02; G01N 31/00

[52] U.S. Cl. .................................. 435/4; 435/34; 435/29; 435/41; 435/42; 435/9; 436/10; 436/164; 210/745; 73/61.71; 73/64.43

[58] Field of Search .................................. 435/4, 34, 29, 435/41, 42, 9; 436/10, 164; 210/745; 73/61.71, 64.43

[56] References Cited

U.S. PATENT DOCUMENTS

| | | | |
|---|---|---|---|
| 2,863,354 | 12/1958 | Diehl et al. | 435/34 |
| 3,954,615 | 5/1976 | Shelef | 435/4 |
| 4,066,362 | 1/1978 | Carter | 435/34 |
| 4,220,858 | 9/1980 | Ikeguchi et al. | 422/55 |
| 4,602,348 | 7/1986 | Hart | 435/4 |
| 4,855,061 | 8/1989 | Martin | 422/55 |
| 4,957,624 | 9/1990 | Peranio | 435/4 |
| 5,030,419 | 9/1991 | Ellis et al. | 422/55 |
| 5,032,261 | 7/1991 | Pyper | 435/4 |
| 5,084,165 | 1/1992 | Wang et al. | 422/55 |
| 5,164,085 | 11/1992 | Spokoiny et al. | 435/4 |
| 5,242,602 | 9/1993 | Richardson et al. | 422/55 |
| 5,277,802 | 1/1994 | Goodwin | 435/4 |
| 5,303,026 | 4/1994 | Strobl et al. | 422/55 |
| 5,403,497 | 4/1995 | Schultz | 435/4 |

*Primary Examiner*—John Kight
*Assistant Examiner*—Louis Leary
*Attorney, Agent, or Firm*—Allen, Dyer, Doppelt, Milbrath & Gilchrist, P.A.

[57] ABSTRACT

The method and apparatus for detecting the presence of an organism in a sample of liquid involves collecting an extinction spectrum of liquid sample, deconvoluting the spectrum to obtain a particle size distribution for the sample, comparing the spectrum and the particle size distribution with, respectively, a control spectrum and a control particle size distribution for the organism, and determining from the comparisons whether the organism to be detected is present in the sample. The apparatus and method permit on-line real-time quantitative classification, identification, and viability assessment of an organism such as a harmful microorganism in a water supply line.

8 Claims, 6 Drawing Sheets

EXTINCTION SPECTRA OF CRYPTOSPORIDIUM PARVUM
INDIRECTLY STAINED WITH ab-FITC

EXTINCTION SPECTRA OF GIARDIA LAMBLIA
INDIRECTLY STAINED WITH ab-FITC

C. PARVUM WITH RHODAMINE

EXTINCTION SPECTRA OF CRYPTOSPORIDIUM PARVUM DIRECTLY STAINED WITH ab-RHODAMINE

GIARDIA LAMBLIA WITH RHODAMINE

EXTINCTION SPECTRA OF GIARDIA LAMBLIA DIRECTLY STAINED WITH ab-RHODAMINE

WEIGHT BASED PARTICLE SIZE DISTRIBUTION OF C. PARVUM AND C. BAILEYI.

WEIGHT BASED PARTICLE SIZE DISTRIBUTION OF G. LAMBLIA AND G. MURIS.

METHOD AND APPARATUS FOR THE DETECTION AND CLASSIFICATION OF MICROORGANISMS IN WATER

BACKGROUND OF THE INVENTION

1. Field of the Invention

The present invention relates no the detection of organisms in liquids, and, more particularly, to the spectrophotometric detection of microorganisms in aqueous solutions.

2. Description of Related Art

Water quality is an extremely important environmental issue, particularly as regards the quality of drinking water. The number and size of the particulate matter suspended in drinking water is continuously monitored after the filtration units in water treatment facilities, specifically to detect the presence of microorganisms such as enteroviruses, protozoa, and bacteria capable of presenting serious health hazards.

The enteric protozoa Cryptosporidium and Giardia are known to cause waterborne diseases, even when present in fairly dilute concentrations. Giardia is the most frequently identifiable agent responsible for such diseases in the United States; Cryptosporidium has caused outbreaks in the United Kingdom as well as the United States and is now recognized as being one of the most disinfectant-resistant waterborne pathogens known. These occurrences have emphasized the need for rapid detection techniques or contaminants in source and treated water.

Currently there is no on-line instrumentation capable of detecting, counting, and classifying specific microorganisms. The technology known in the art requires that the particulate matter suspended in the water be concentrated and then detected with the use of microscopic techniques. Such laboratory techniques include immunofluorescent assay (IFA), polymerase chain reaction (PCR), flow cytometry (FC), and cell sorting. IFA technology may be used in conjunction with microscopy for identification following labeling with specific antibodies. The limitations associated with IFA include long analysis times, an inability to detect viability and to distinguish between species, and low sensitivity. The disadvantages of PCR include environmental interference, long analysis times, and an inability to quantify organisms. FC has the disadvantages of high instrumentation costs, high level of training of personnel required, an inability to distinguish between species, and small sample volumes.

In industrial settings, detection methods include turbidity and particle counting. Turbidity is known as a technique for evaluating filter efficiency and water quality and can be used on line. Standard turbidity measurements respond to both particle size and number; therefore, they do not distinguish between the two. Liquid-borne particle counters (LPC) illuminate a very small sample volume for analysis and have not traditionally been used for on-line applications. Although LPC cannot differentiate between species, if coupled with adequate sampling strategies, particle counters can be used effectively for on-line applications.

As is known from spectroscopy theory, a measure of the absorption of a solution is the extinction coefficient, which also provides a measure of the turbidity. Spectra in the visible region of the electromagnetic spectrum reflect the presence of metal ions and large conjugated aromatic structures double-bond systems. In the near-uv region small conjugated ring systems affect absorption properties. However, suspensions of very large particles are powerful scatterers of radiation, and in the case of microorganisms, both light scattering and absorption effects are sufficiently strong to permit quantitative detection and classification. It is therefore known to use uv/vis spectroscopy to monitor purity, concentration, and reaction rates of such large molecules.

Many attempts have been made to estimate the PSD and the chemical composition of suspended particles using optical spectral extinction (turbidity) measurements. However, previously used techniques require that either the form of the PSD be known a priori or that the shape of the PSD be assumed. The present inventor has applied standard regularization techniques to the solution of the turbidity equation and has demonstrated correct PSDs of a large variety of polymer lattices, protein aggregates, silicon dioxide particles, and microorganisms.

SUMMARY OF THE INVENTION

It is therefore an object of the present invention to provide a spectroscopic and turbidimetric technique for the identification and classification of microorganisms in a liquid medium.

It is a further object to provide on-line instrumentation capable of detecting, counting, and classifying particulates in an aqueous medium.

It is an additional object to provide such instrumentation having at least 2 nanometer resolution.

It is another object to provide a technique capable of detecting the viability of microorganisms present in a liquid medium.

It is yet a further object to provide a monitoring technique for drinking water to prevent the passage of waterborne pathogens into the drinking water supply.

These and other objects are addressed by the apparatus and method of the present invention for detecting the presence of an organism in a sample of liquid. The method comprises the steps of collecting an extinction spectrum over a predetermined range of wavelengths of the sample of liquid and then deconvoluting the spectrum to obtain a particle size distribution for the sample. The wavelength range generally comprises the entire ultraviolet/visible (uv/vis) range, from 180 to 900 nm. In a particular embodiment, however, the spectrum is collected over the wavelength range of 400 to 820 nm. Previously used systems have used a single frequency to classify organisms, whereas in the present invention the whole spectrum is solved to obtain a self-consistent solution. The spectrum and the particle size distribution are then compared with, respectively, a control spectrum and a control particle size distribution for the organism. From these comparisons it can be determined from the comparisons whether the organism to be detected is present in the sample.

An additional embodiment of the method, used for particle counting applications, further comprises the step of determining the quantity of the organism to be detected in the sample from the particle size distribution.

Yet another embodiment entails determining the viability of the organism to be detected in the sample from the particle size distribution.

The apparatus of the present invention comprises means for performing the above-listed steps. In a particular embodiment, the spectrum collecting means comprises a spectrophotometer.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–9.

Figure 8:
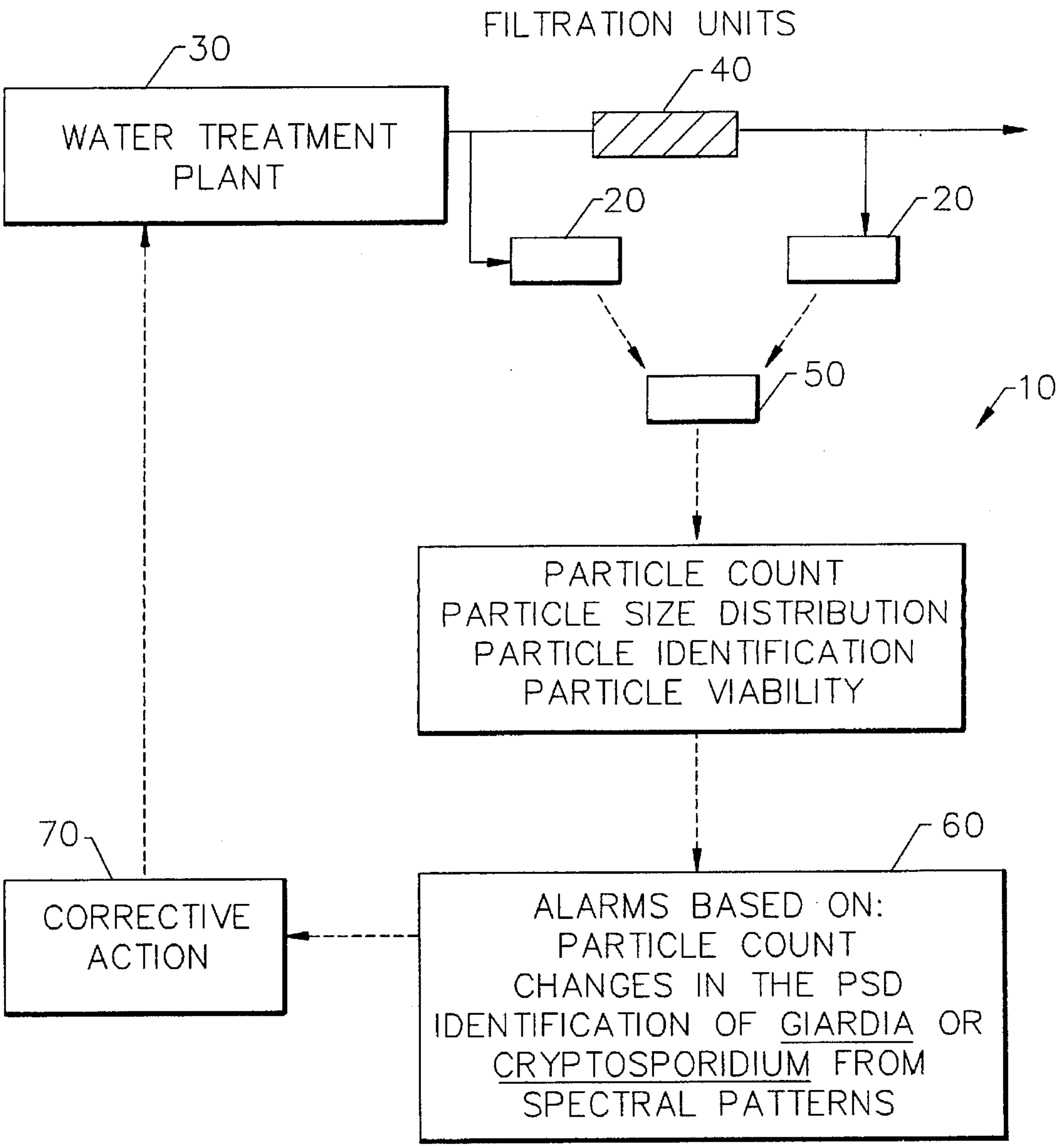
FIG. 8 is a block diagram of the system configuration.

The apparatus 10 and method of using same for detecting the presence of an organism in a sample of liquid are depicted in FIG. 8. In the particular embodiment to be treated herein for microorganisms, the protozoa *Cryptosporidium parvum* and *Giardia lamblia* in aqueous dispersion are detected through spectroscopic means over a predetermined wavelength range. In this embodiment, shown in FIG. 8 for the detection of the protozoa at a water treatment plant 30 having a filtration unit 40, a uv/vis extinction spectrum is collected with a pair of spectrophotometers/turbidimeters 20, one upstream of the filtration unit 40 and one downstream of the filtration unit 40 over the predetermined wavelength range is generally 400–820 nm. Three exemplary spectrophotometers that may be utilized comprise an Ocean Optics S-1000 miniature diode array spectrophotometer, a Hewlett-Packard 8452A diode array spectrophotometer, and a Perkin Elmer 3840 uv/vis spectrometer.

The measurements reported herein were conducted at room temperature in a 1-cm-path-length cell. Prior to collecting a spectrum, it should be determined whether the water sample is in a linear range of the spectrophotometer 20. If necessary, the water sample is diluted with a background solution to reach the linear range of the spectrophotometer 20. The data are then transmitted to a computer 50, which is configured in this exemplary embodiment to perform analytical tasks such as data processing, to issue alarms, and to issue signals for control action.

A spectrum obtained in this manner is then corrected for background. The average refractive index of the protozoa was approximated as 1.386 and was assumed constant as a function of wavelength. The refractive index of water as a function of wavelength was calculated from previously published data.

Figure 1:
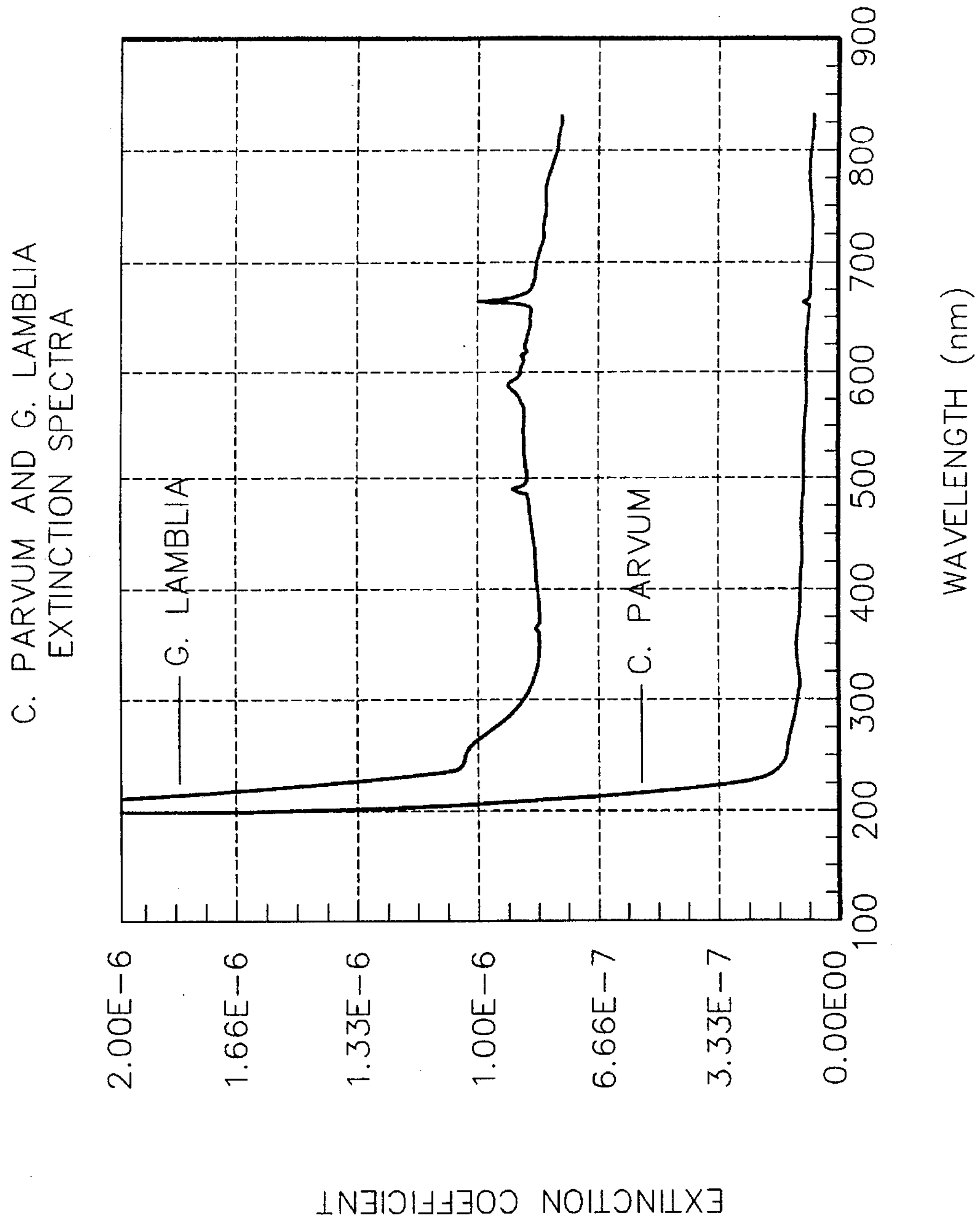
FIG. 1 shows extinction spectra for *Cryptosporidium parvum* and *Giardia lamblia.*

Exemplary extinction spectra of *Giardia lamblia* and *Cryptosporidium parvum* are shown in FIG. 1. *C. parvum* is known to be spherical and to have a size of approximately 4–5 μm; *G. lamblia* is ovoid, with a length of approximately 10–15 μm and a width of 6–10 μm. These spectra are typical of purified samples diluted with formalin.

A tail trailing toward longer wavelengths can be seen in FIG. 1, indicating the presence of particulate matter. The greater intensity of the *G. lamblia* spectrum as compared with that of *C. parvum* is due to the greater scattering caused by the greater size of *G. lamblia.*

Comparison of the spectra in the wavelength region 200–400 nm indicates that there are spectral features that are usable for identification and classification purposes. It is known that staining a microorganism prior to collecting the spectrum can improve the sensitivity of spectroscopy measurements. Two stains that have been utilized on the protozoa under examination are ab-FITC complex and ab-rhodamine.

Figure 2:
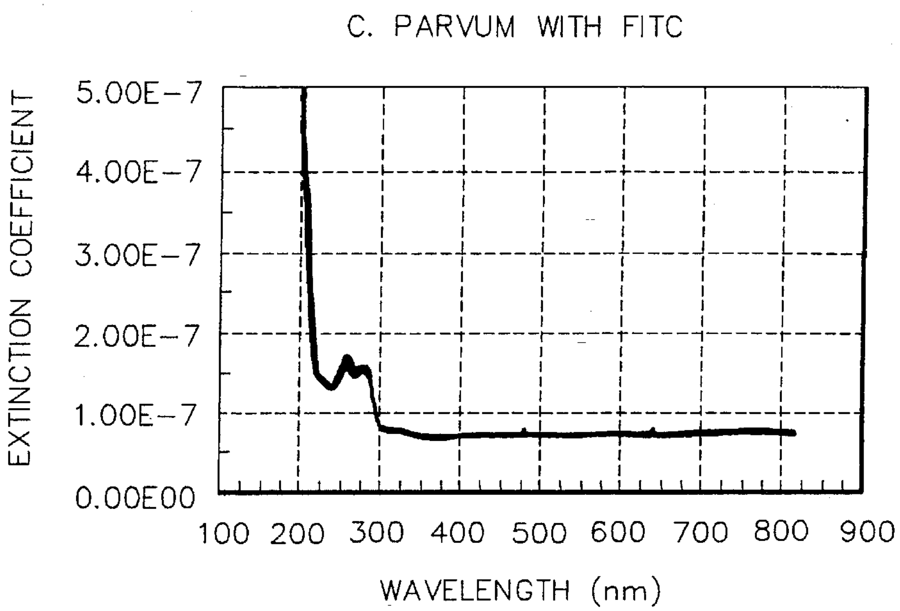
FIG. 2 shows extinction spectra for *Cryptosporidium parvum* indirectly stained with ab-FITC.
Figure 3:
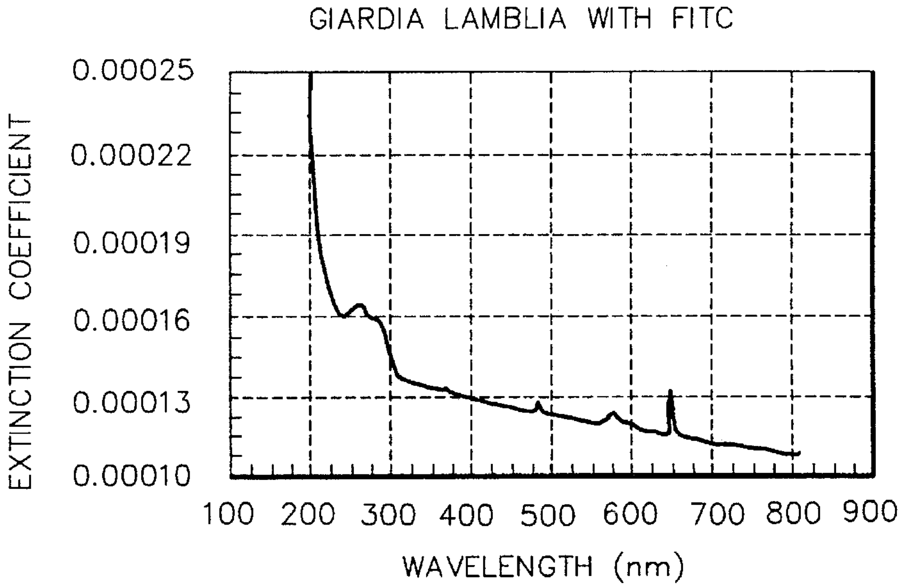
FIG. 3 shows extinction spectra for *Giardia lamblia* indirectly stained with ab-FITC.

FIGS. 2 and 3 show the extinction spectra of *C. parvum* and *G. lamblia*, respectively, indirectly stained with ab-FITC complex, which fluoresces apple-green (the wavelength is in the general range of 300 nm; however, scattering and absorption will cause a shift in the pattern, making these numbers approximate). FITC has been known in the art for use by microscopists and can enable detection of fewer than ten organisms per milliliter from a purified stock. A comparison of the spectra in FIG. 1 with those in FIGS. 2 and 3 clearly indicates that staining with ab-FITC enhances the sensitivity of the spectroscopic measurements. In addition, the use of staining allows a direct comparison between the present results and previous microscopy analysis. It can also be noted that other features of the spectra are retained, with *G. lamblia* having a higher intensity in the visible range, due to its larger size.

Figure 4:
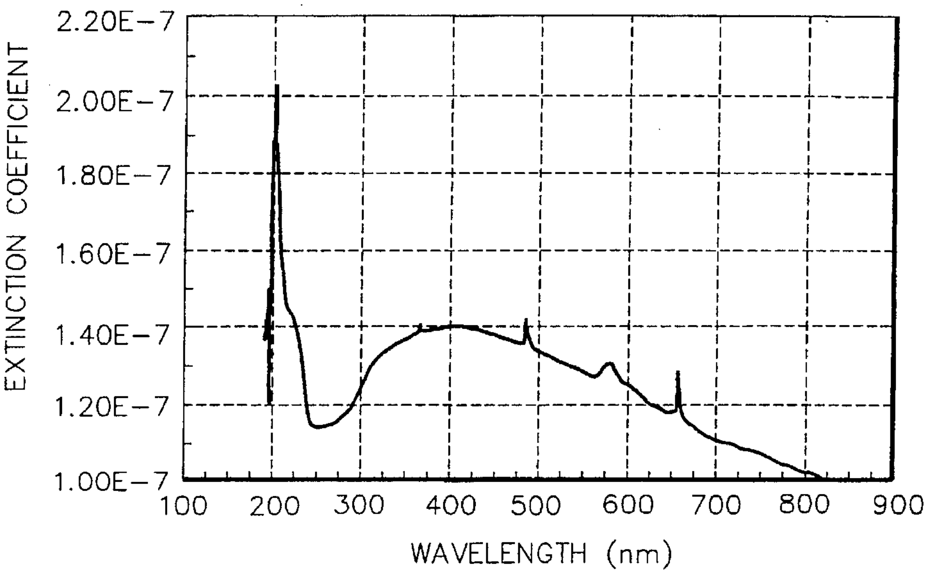
FIG. 4 shows extinction spectra for *Cryptosporidium parvum* directly stained with ab-rhodamine.
Figure 5:
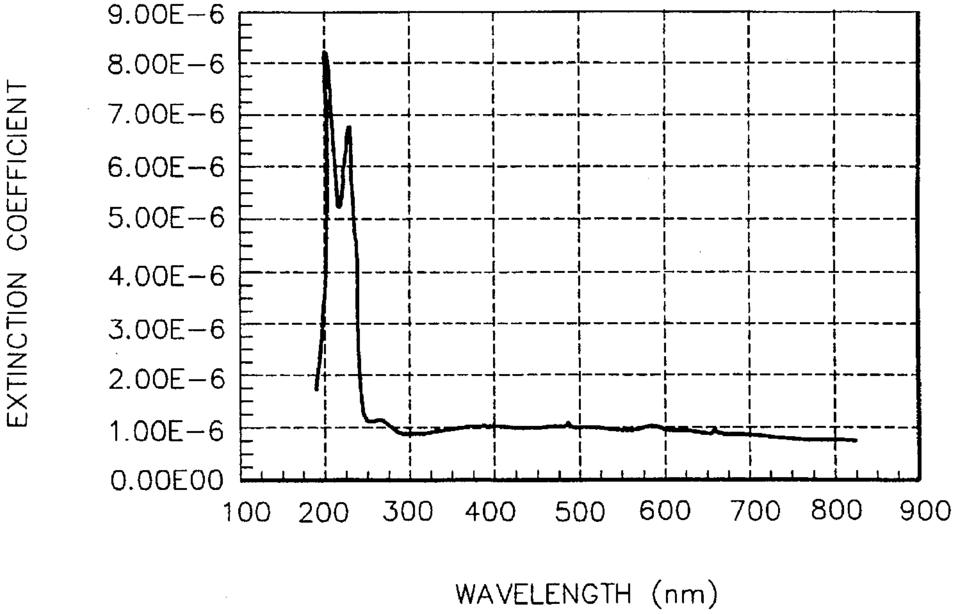
FIG. 5 shows extinction spectra for *Giardia lamblia* directly stained with ab-rhodamine.

FIGS. 4 and 5 show the extinction spectra of *C. parvum* and *G. lamblia* stained with ab-rhodamine. This stain, which is red (as above for ab-FITC, an approximate wavelength range is generally 400 nm), is known for use in microscopy studies. A comparison of FIGS. 1–5 indicates that the distribution of stains is different for the two protozoa and that, in addition to enhancing the signal, the use of stains greatly facilitates the identification and classification of microorganisms.

The collection of spectra such as shown in FIGS. 1–5 therefore permits an identification of microorganisms based on spectral signature; that is, the sample spectrum can be compared with a control spectrum for the organism to determine whether the organism is present in the water sample.

A spectrum collected as discussed above is then analyzed with the use of computation means 50, which comprises a computer having software for deconvoluting the spectrum to obtain a particle size distribution for the sample.

Figure 9:
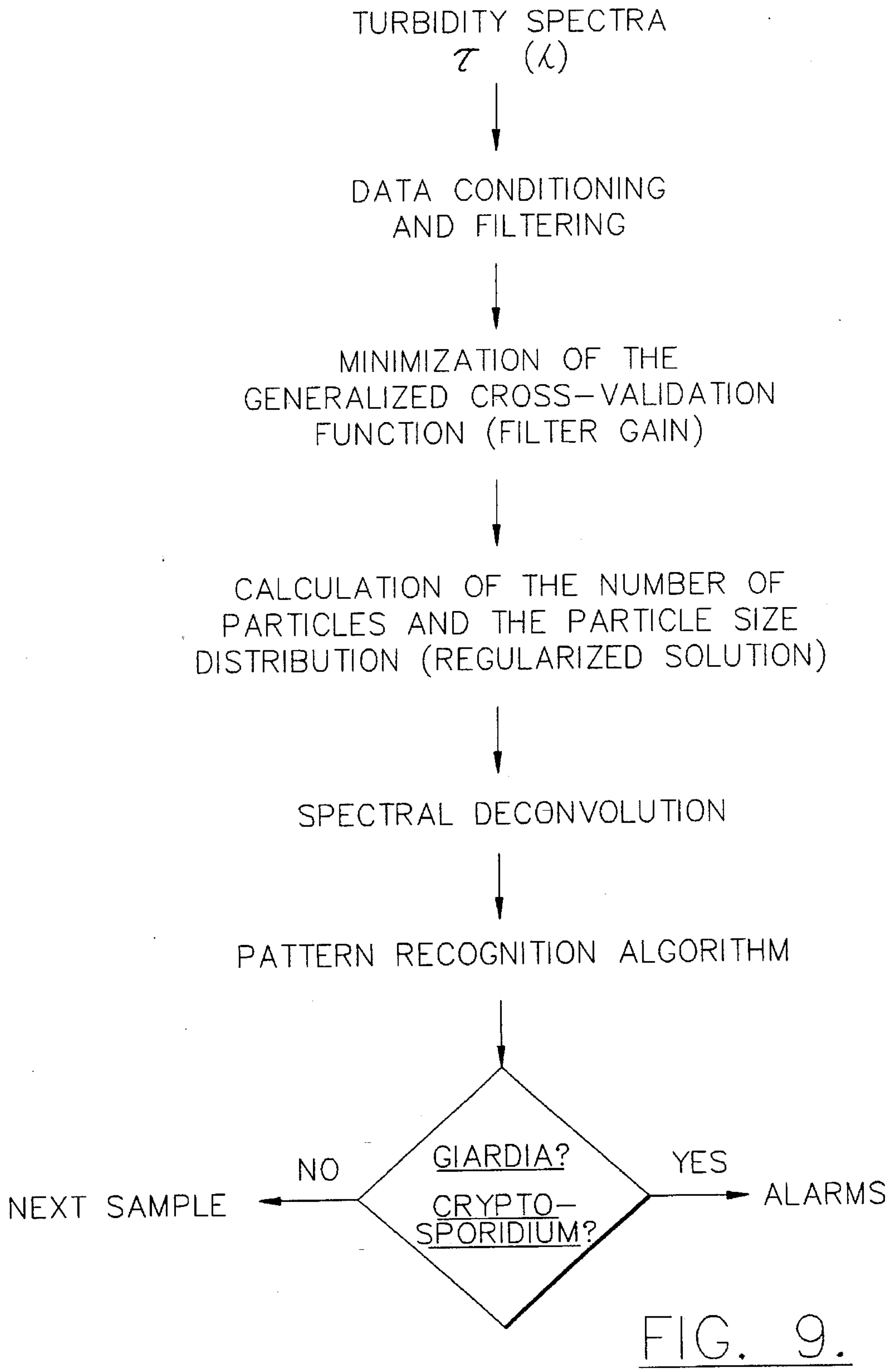
FIG. 9 is a flow chart of the data analysis method.

The present inventor has devised a technique for determining a discretized particle size distribution from turbidity spectra, shown diagrammatically in FIG. 9. The equations providing the theoretical framework are developed from a relation between the turbidity as a function of wavelength $\tau(\lambda_0)$ and the normalized particle size distribution f(D):

$$\tau(\lambda_0) = N_p(\pi/4) \int_0^\infty Q(\lambda_0, D)\, D^2 f(D)\, dD, \quad (1)$$

where D is the effective particle diameter, $Q(\lambda_0, D)$ corresponds to the Mie scattering coefficient, and $N_p$ is the number of particles per unit volume. Equation (1) can be written in matrix form by discretizing the integral with an appropriate quadrature approximation:

$$\tau = A f + \epsilon, \quad (2)$$

where $\epsilon$ represents both experimental errors and errors due to the model and the discretization procedure. The regularized solution to Eq. (2) is given by:

$$f(\gamma) = (A^T A + \gamma H)^{-1} A^T \tau, \quad (3)$$

where H is a covariance matrix that essentially adaptively filters the experimental and the approximation errors ($\epsilon$), and $\gamma$ is the regularization parameter estimated using the generalized cross-validation technique. This technique requires the minimization of the following objective function with respect to $\gamma$:

$$V(\gamma) = m\|[I - A(A^T A + \gamma H)^{-1}]\tau\|^2 / Tr\{[I - A(A^T A + \gamma H)^{-1}]A^T\}^2 \quad (4)$$

A simultaneous applications of Eqs. (3) and (4) to the measured turbidity spectra yields the discretized particle size distribution. The corrected scattering spectra can then be used for composition analysis and/or to fingerprint the absorption characteristics of particles.

Figure 6:
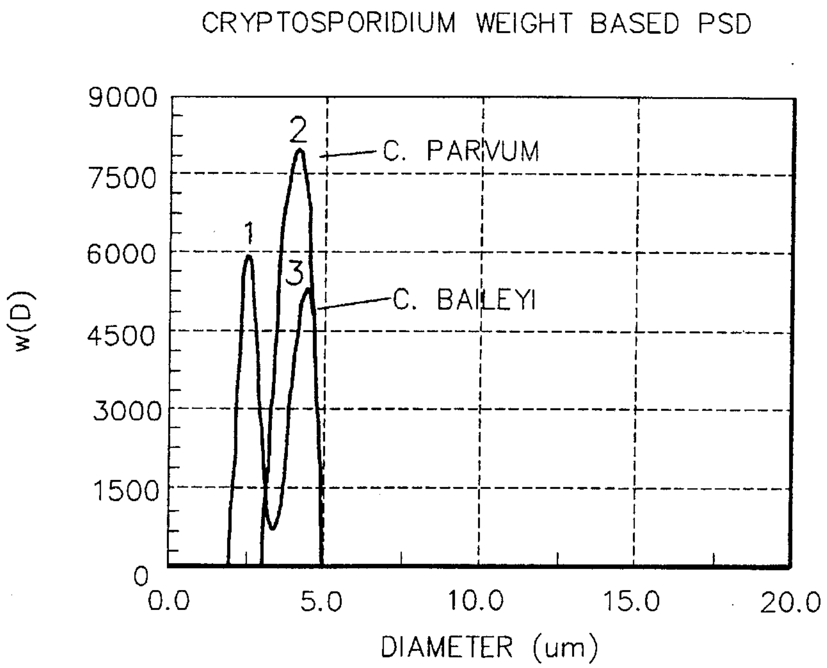
FIG. 6 is a weight-based particle size distribution of *C. parvum* and *C. baileyi.*
Figure 7:
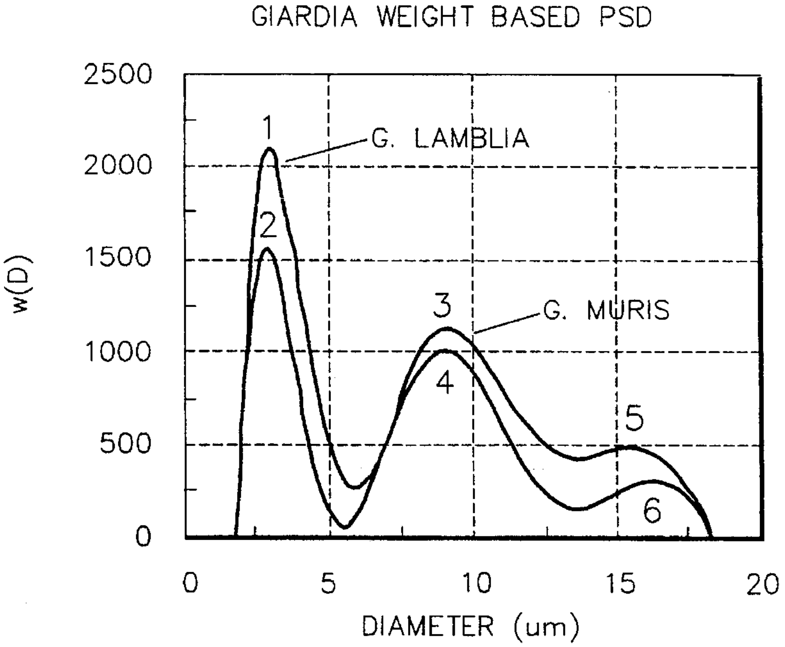
FIG. 7 is a weight-based particle size distribution of *G. lamblia* and *G. muris.*

Quantitative information, such as shown in FIGS. 6 and 7, may be obtained using the method of the present invention from the use of Eqs. (3) and (4) and spectra such as shown in FIG. 1.

FIG. 6 shows a weight-based particle size distribution (PSD) for *C. parvum* (peak 2) and *C. baileyi* (peaks 1 and 3). Peaks 2 and 3 are centered around 4.8 μm, the size normally associated with *C. parvum*. The difference between the two samples is seen at peak 1, which is centered at 2.5 μm. By deconvoluting the extinction spectra of the purified samples, the PSD was obtained. The abscissa represents the diameter of the microorganisms, and the ordinate, the weight-based density. Peak 1 is indicative of cell debris from broken oocysts and sporozoites; the *C. parvum* sample was purified by high-performance liquid chromatography, whereas the *C. baileyi* sample was not.

FIG. 7 shows the PSD for *G. muris* (peaks 1, 4, and 6), and *G. lamblia* (peaks 2, 3, and 5). Peaks 1 and 2, approximately located at 2.8 μm, are indicative of cell debris resulting from the preparation of the samples. Peaks 3 and 4 are located at approximately 9.0 μm and correspond to typical dimensions of both *G. lamblia* and *G. muris*. Peaks 5 and 6, centered at approximately 16 μm, correspond to cell aggregates and/or cells oriented perpendicular to the incident light.

Utilizing the above method to calculate the particle size distribution, the PSD can then be compared with a control particle size distribution for the organism, and then one can determine from the comparison whether the organism to be detected is present in the sample.

These calculations can also be used to determine the quantity of the organism to be detected in the sample from the particle size distribution.

Another embodiment of the method of the present invention comprises determining the viability of the organism to be detected in the sample from the particle size distribution. In this embodiment staining would again be used, with the stain uptake providing an indication of particle viability, for instance. This technique could also be performed on-line.

A particular use for the apparatus and method of the present invention is for on-line, real-time measurements to detect the presence of an organism in a flowing liquid. In order to accomplish this, a sample is taken from the flowing liquid, and an extinction spectrum is collected over a predetermined range of wavelengths of the sample of liquid, the spectrum being collected at the site of the sample collection. Staining may also be used as described above.

As previously the spectrum is deconvoluted to obtain a particle size distribution for the sample, and the spectrum and the particle size distribution are compared with, respectively, a control spectrum and a control particle size distribution for the organism. From these comparisons it can be determined whether the organism to be detected is present in the sample.

Also as previously, the quantity and the viability of the organism to be detected in the sample can be determined from the particle size distribution.

It is contemplated that such an on-site apparatus could be placed in communication with virtually any water line, including at an entrance to a dwelling. Should harmful particles be detected, an alarm 60 could ring, as shown in FIG. 8 for a water treatment plant 30, indicating that the water flowing through the system was unsafe. Corrective action 70 would then be taken, such as shutting down the water flow at the plant, and the water could be subjected to additional purification prior to proceeding downstream.

It may be appreciated by one skilled in the art that additional embodiments may be contemplated, including systems and methods for detecting other types of organisms and particles in a liquid, for studying and monitoring organism life cycles, for examining drug delivery mechanisms, for studying the mechanisms of infectious diseases, and for detecting abnormal cells.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for detecting the presence of an microorganism in a sample of liquid, the method comprising the steps of:

collecting an extinction spectrum over a predetermined range of wavelengths of the sample of liquid;

deconvoluting the spectrum to obtain a particle size distribution for the sample;

comparing the spectrum and the particle size distribution with, respectively, a control spectrum and a control particle size distribution for the microorganism; and determining from the comparisons whether the microorganism to be detected is present in the sample.

2. The method for detecting the presence of an microorganism recited in claim 1, further comprising the step of determining the quantity of the microorganism to be detected in the sample from the particle size distribution.

3. The method for detecting the presence of an microorganism recited in claim 1, further comprising the step of determining the viability of the microorganism to be detected in the sample from the particle size distribution.

4. The method for detecting the presence of an microorganism recited in claim 1, wherein the collecting step comprises collecting an extinction spectrum over a wavelength range of 400 to 820 nm.

5. A method for spectrophotometrically detecting the presence of a microorganism in a water sample, the method comprising the steps of:

determining whether the water sample is in a linear range of the spectrophotometer;

diluting the water sample if necessary with a background solution to reach the linear range of the spectrophotometer;

using the spectrophotometer to collect a turbidity spectrum of the water sample over the wavelength range of 400 to 820 nm;

correcting the spectrum for background;

calculating a particle size distribution from the corrected spectrum;

comparing the particle size distribution with a known particle size distribution for the microorganism to be detected; and determining from the comparison whether the microorganism is present in the water sample.

6. The method recited in claim 5, further comprising the step of staining the microorganism prior to collecting the turbidity spectrum for improving sensitivity.

7. The method recited in claim 5, further comprising the step of quantifying, from the particle size distribution, the number of microorganisms present in the water sample.

8. The method recited in claim 5, further comprising the step of determining, from the particle size distribution, the viability of the microorganisms present in the water sample.

* * * * *

UNITED STATES PATENT AND TRADEMARK OFFICE

CERTIFICATE OF CORRECTION

PATENT NO. : 5,616,457

DATED : April 1, 1997

INVENTOR(S) : Luis Humberto Garcia Rubio

It is certified that error appears in the above-identified patent and that said Letters Patent is hereby corrected as shown below:

Column 1, Line 6 Insert:

This invention was made with U. S. Government support under NSF Grant RII-850-756 awarded by the Department of the Navy. The Government has certain rights in the invention.--

Signed and Sealed this

Third Day of March, 1998

Attest:

BRUCE LEHMAN

Attesting Officer

Commissioner of Patents and Trademarks